United States Patent [19]

Shimizu et al.

[11] 4,444,882
[45] Apr. 24, 1984

[54] PROCESS AND APPARATUS FOR CONTROLLING CULTIVATION OF MICROORGANISMS

[75] Inventors: Norio Shimizu; Tetsuo Yamaguchi; Setsuo Saitou; Masao Ueno; Yooji Odawara, all of Hitachi, Japan

[73] Assignee: Hitachi, Ltd., Tokyo, Japan

[21] Appl. No.: 324,550

[22] Filed: Nov. 24, 1981

[30] Foreign Application Priority Data

Nov. 26, 1980 [JP] Japan .................. 55-165240
Jan. 21, 1981 [JP] Japan .................... 56-6332
Mar. 4, 1981 [JP] Japan ................... 56-29931

[51] Int. Cl.³ ............................................ C12Q 1/29
[52] U.S. Cl. .................................. 435/29; 435/256; 435/813
[58] Field of Search ............... 435/3, 315, 289, 291, 435/807, 818, 819, 29, 256, 813

[56] References Cited

U.S. PATENT DOCUMENTS 3,929,582 12/1975 Kellner .................. 435/3

FOREIGN PATENT DOCUMENTS 775122 10/1980 U.S.S.R. .................. 435/3

*Primary Examiner*—Ferris H. Lander
*Attorney, Agent, or Firm*—Mary Louise Beall

[57] ABSTRACT

Cultivation of microorganisms is controlled by measuring a pressure in a cultivation tank, a flow rate of effluent gas from the cultivation tank, and a concentration of carbon dioxide gas in the effluent gas, calculating a partial pressure of carbon dioxide gas in the cultivation tank and an amount of a carbon dioxide gas produced by the microorganisms, calculating an amount of propagated microorganism cells from the resulting partial pressure of carbon dioxide gas and the amount of produced carbon dioxide gas, thereby calculating an amount of microorganism cells in culture liquor, and supplying a substrate in an amount controlled in accordance with the resulting amount of microorganism cells in culture liquor.

Microorganisms can be cultivated in high yield and at a high product concentration.

8 Claims, 9 Drawing Figures

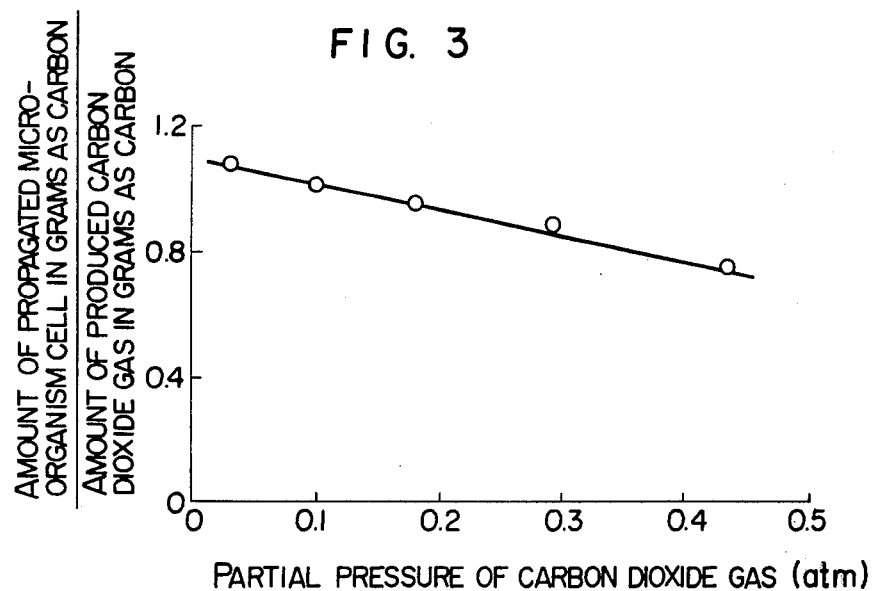
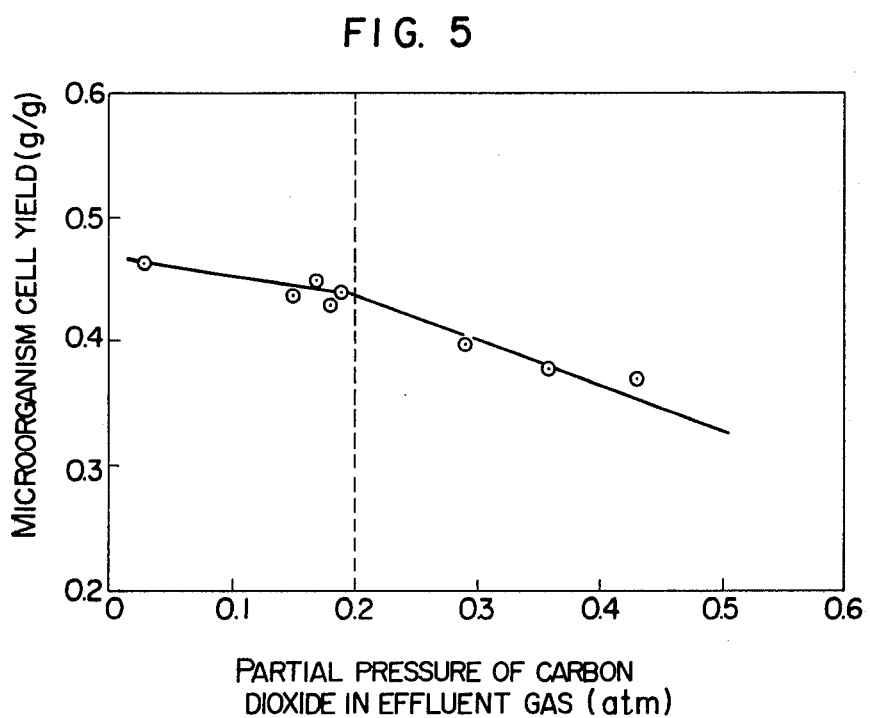

PROCESS AND APPARATUS FOR CONTROLLING CULTIVATION OF MICROORGANISMS

The present invention relates to a process and an apparatus for controlling cultivation of microorganisms by calculating the amount of microorganism cells in culture liquor from the partial pressure of carbon dioxide gas in a cultivation tank as an index and the amount of carbon dioxide gas produced by the microorganisms, and supplying a substrate in an amount controlled in accordance with the calculated amount of microorganism cells.

Microorganisms are cultivated by continuously or intermittently supplying a substrate to a cultivation tank. It is the current practice for supplying the substrate to estimate relations between a cultivating time and a preferable amount of substrate to be supplied or a period of time required until the amount of propagated microorganism cells reaches a desired value on the basis of the actual results of cultivation so far obtained as regards the individual microorganisms, substrates, etc., and to prepare a program of supplying a given substrate before cultivation is carried out. However, the microorganisms used in the individual cultivation are not always on an equal activity level, and thus efficient cultivation cannot be carried out by supplying the substrate according to a predetermined program. For example, it is known that when an ethanol-assimilating microorganism or a methanol-assimilating microorganism is cultivated with ethanol or methanol, respectively, as the main carbon source and when a substrate is supplied in excess, propagation of microorganism cells is inhibited, whereas, when the substrate is supplied insufficiently, propagation of microorganism cells is suppressed.

It is also known that, when bread yeast is cultivated with sugar as the main carbon source, and when a substrate is supplied in excess, the bread yeast starts to convert the sugar to ethanol, lowering a yield based on the sugar (ratio of the amount of propagated cells to the amount of the supplied substrate), whereas, when the substrate is supplied insufficiently, propagation of bread yeast is suppressed, lowering productivity per unit volume of a cultivation tank and per unit time.

As is obvious from the foregoing examples of cultivation, it is important in the cultivation process to rapidly determine the amount of microorganism cells in culture liquor and supply the substrate in an amount controlled on the basis of the determined amount of the microorganism cells and thereby efficiently conduct the cultivation process.

The amount of microorganism cells in culture liquor can be determined according to a procedure of separating microorganism cells by centrifuging or filtering a portion of culture liquor, drying the separated microorganism cells at about 110° C. for a prolonged time, and measuring the weight of dried cells, or a procedure of sampling a portion of culture liquor and counting the number of microorganism cells by microscope, or a procedure of measuring the turbidity of culture liquor, thereby estimating the concentration of microorganism cells, or a procedure of estimating the amount of microorganism cells from a consumption rate of oxygen or from a production rate of carbon dioxide gas.

However, the procedure of measuring the weight of dried microorganism cells has such a problem that it takes more than 10 hours from the time of sampling the culture liquor to the time of obtaining the result of measurement, and the procedure of counting the number of microorganism cells has a problem of a large fluctuation in the counts. Thus, the amount of microorganism cells in culture liquor cannot be determined rapidly and exactly, and the substrate cannot be supplied in an amount controlled in accordance with the determined amount of microorganism cells in these two procedures.

The procedure of estimating the concentration of microorganism cells from a turbidity is based on such a prerequisite that culture liquor be clear, but in the most cases of actual commercial cultivation, culture liquor is considerably colored and contains other solid matters than the microorganism cells, so that it is difficult to exactly determine the concentration of microorganism cells. Thus, the procedure fails to supply the substrate in an amount controlled in accordance with the amount of microorganism cells owing to poor reliability of resulting concentration.

The procedure of estimating the amount of microorganism cells from a consumption rate of oxygen or a production rate of carbon dioxide gas is based on an assumption that the consumption rate of oxygen or production rate of carbon dioxide gas per unit amount of microorganism cells is constant, but these rates are greatly influenced by circumstances, particularly by the partial pressure of carbon dioxide gas, and thus are not constant. The procedure fails to determine the amount of cells exactly.

A procedure for determining the amount of microorganism cells in culture liquor rapidly and exactly has been so far unknown in the cultivation of microorganisms, as described above. That is, a process for controlling cultivation of microorganisms by supplying a substrate in an amount controlled in accordance with the amount of microorganism cells in culture liquor.

SUMMARY OF THE INVENTION

An object of the present invention is to provide a process for controlling cultivation of microorganisms capable of always maintaining better conditions for supplying a substrate or maintaining high yield of product.

The present invention is based on such a fact found by the present inventors that there is a proportional relation between the amount of produced carbon dioxide gas and the amount of propagated microorganism cells in cultivation of microorganisms, and a ratio of the amount of propagated microorganism cells to the amount of produced carbon dioxide gas depends upon the partial pressure of carbon dioxide gas in a cultivation tank.

The present invention provides a process for controlling cultivation of microorganisms, which comprises measuring a pressure in a cultivation tank, a flow rate of effluent gas from the cultivation tank, and a concentration of carbon dioxide gas in the effluent gas, calculating a partial pressure of carbon dioxide gas in the cultivation tank and an amount of a carbon dioxide gas produced by the microorganisms, calculating an amount of propagated microorganism cells from the resulting partial pressure of carbon dioxide gas and the amount of produced carbon dioxide gas, thereby calculating an amount of microorganism cells in culture liquor, and supplying a substrate in an amount controlled in accordance with the resulting amount of microorganism cells in culture liquor.

The present process is carried out in an apparatus for controlling cultivation of microorganisms which comprises a combination of means of measuring a pressure in a cultivation tank, a means of measuring a flow rate of an effluent gas from the cultivation tank, a means of measuring a concentration of carbon dioxide gas in the effluent gas, a means of calculating a partial pressure of carbon dioxide gas in the cultivation tank and an amount of carbon dioxide gas produced by microorganisms from the resulting pressure value, flow rate value and concentration of carbon dioxide gas, thereby calculating an amount of microorganism cells, a means of determining an amount of a substrate to be supplied from the resulting amount of microorganism cells, a means of setting numerical values for the means of calculating the partial pressure, amount of carbon dioxide gas, and amount of microorganism cells, and a means of controlling an amount of a substrate to be supplied in function with the determined amount of the substrate to be supplied.

According to the present invention, a substrate is supplied in an amount controlled in accordance with an amount of microorganism cells in culture liquor by calculating a partial pressure of carbon dioxide gas in a cultivation tank, determining an amount of produced carbon dioxide gas at desired time intervals, determining an amount of propagated microorganism cells at the time intervals from a ratio of the amount of propagated microorganism cells to the amount of produced carbon dioxide gas in accordance with the partial pressure of carbon dioxide gas, calculating the amount of entire microorganism cells in culture liquor, and supplying a substrate in an amount controlled in accordance with the amount of microorganism cells on the basis of the calculated amount of microorganism cells in culture liquor.

The present process for controlling cultivation of microorganisms with an oxygen-enriched gas is characterized by controlling a correlation between a critical partial pressure of carbon dioxide gas in a relation between yield and partial pressure of carbon dioxide gas, and an amount of dissolved oxygen in combination with an aeration rate of an oxygen-enriched gas, its oxygen concentration and number of revolution per minutes of stirrer.

It can be seen that the amount of microorganism cells in culture liquor can be calculated rapidly and exactly by the partial pressure of carbon dioxide gas in a cultivation tank as an index according to the present invention, and further the amount of a substrate to be supplied can be rapidly controlled on the basis of the calculated amount of microorganism cells, and consequently the yield of microorganism cells or product can be maintained in a high level throughout the cultivation.

According to the present invention, the partial pressure of carbon dioxide in the effluent gas and the amount of dissolved oxygen can be appropriately controlled by changing an aeration rate of oxygen-enriched gas, its oxygen concentration and number of revolution per minute of stirrer in combination, so that microorganisms can be cultivated in high yield of product, for example, microorganism cells in bread yeast or fermentation product in fermentation of inosinic acid, etc. at a high product concentration.

BRIEF DESCRIPTION OF THE DRAWINGS

FIG. 3 is a diagram showing relations between the ratio of the amount of propagated microorganism cells to the amount of produced carbon dioxide gas and the partial pressure of carbon dioxide gas in a cultivation tank.

FIG. 5 is a diagram showing relations between the partial pressure of carbon dioxide in an effluent gas and the yield of microorganism cells in bread yeast cultivation.

FIG. 7($b$) is a diagram showing relations between the cultivation time and the concentration of oxygen in an effluent gas. FIG. 7($c$) is a diagram showing relations between the cultivation time and the number of revolution per minute of stirrer.

DETAILED DESCRIPTION OF THE PREFERRED EMBODIMENTS

Figure 1:
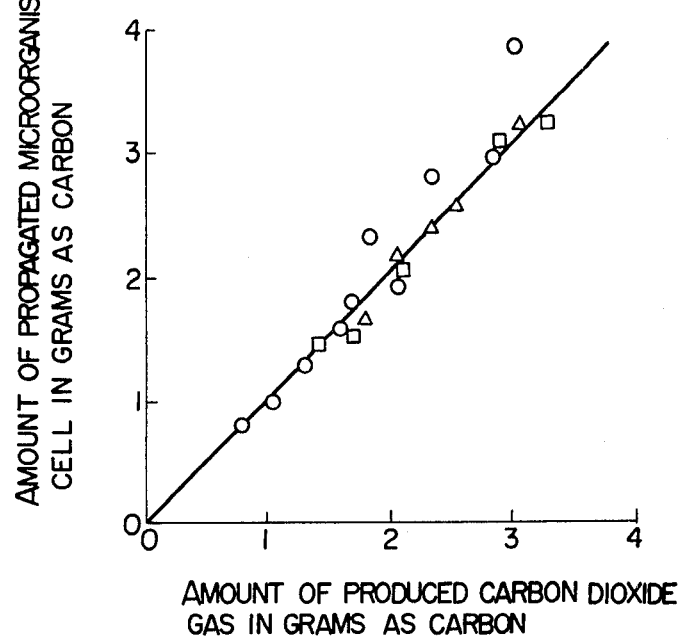
FIG. 1 is a diagram showing relations between the amount of produced carbon dioxide gas and the amount of propagated microorganism cells, where units are given in grams calculated as carbon.

In FIG. 1 relations between the amount of produced carbon dioxide gas and the amount of propagated microorganism cells are shown where bread yeast is cultivated with sugar as the main carbon source under a controlled partial pressure of carbon dioxide gas of 0.1 atm in a cultivation tank, and marks O, Δ and □ show Tests 1, 2 and 3, respectively. As is evident from FIG. 1, the ratio of the propagated microorganism cells to the produced carbon dioxide gas is constant, i.e. 1.0, in terms of carbon balance, for any time intervals throughout the cultivation, where one time interval is set for one hour of cultivation, and units for the axes of abscissa and ordinate are in grams as carbon.

Figure 2:
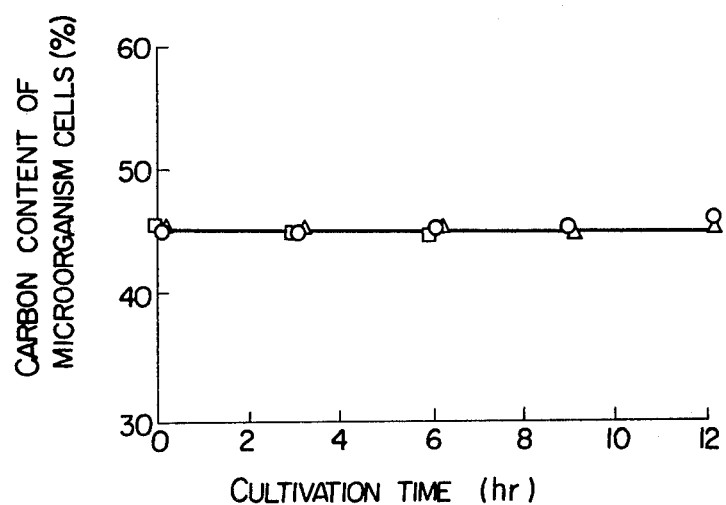
FIG. 2 is a diagram showing changes of the amount of carbon in microorganism cells with time throughout cultivation.

The carbon content of microorganism cells in the above cultivation is constant, i.e. 45%, with cultivation time throughout the cultivation, as is evident from FIG. 2 showing relations between the carbon content of microorganism cells and the cultivation time in Tests 1, 2 and 3.

Tests 1, 2 and 3 shown in FIGS. 1 and 2 were carried out by changing control of the amount of sugar to be supplied against the amount of microorganism cells, where cultivation was conducted while supplying the sugar in an amount controlled to 0.29 g glucose/g dry cell·hr for Test 1, 0.37 g glucose/g dry cell·hr for Test 2 and 0.43 g glucose/g dry cell·hr for Test 3.

Relations between the partial pressure of carbon dioxide gas in a cultivation tank and the ratio of the amount of propagated microorganism cells to the amount of produced carbon dioxide gas are shown in FIG. 3, where it is clearly shown that the ratio of the amount of propagated microorganism cells to the amount of produced carbon dioxide gas depends upon the partial pressure of carbon dioxide gas.

It can be seen from the foregoing that, when the partial pressure of carbon dioxide gas in a cultivation tank and the amount of produced carbon dioxide gas are determined by measuring the pressure prevailing in the cultivation tank, the flow rate of effluent gas from the cultivation tank, and the concentration of carbon dioxide gas in the effluent gas, the amount of microorganism cells in culture liquor can be calculated therefrom according to the following equation.

$$X_2 = X_1 + k\Delta CO_2$$

wherein $X_2$: amount of microorganism cells in culture liquor at the time $t_2$ (g)

$X_1$: amount of microorganism cells in culture liquor at the time $t_1$ (g)

$\Delta CO_2$: amount of carbon dioxide gas produced during the period between the time $t_1$ and the time $t_2$ k: ratio of the amount of propagated microorganism cells to the amount of produced carbon dioxide gas (which depends upon the partial pressure of carbon dioxide gas in a cultivation tank)

In order to calculate the amount of microorganism cells in the present invention, it is necessary to determine relations between the partial pressure of carbon dioxide gas in a cultivation tank and the ratio of the amount of propagated microorganism cells to the amount of produced carbon dioxide gas. The relations depend upon strains and substrates used, but should be determined in advance by carrying out batch cultivation tests and continuous cultivation tests.

No means is available for directly measuring the partial pressure of carbon dioxide gas in a cultivation tank, but in the present invention not only the partial pressure of carbon dioxide gas in a cultivation tank but also the amount of produced carbon dioxide gas by microorganisms can be calculated by measuring the pressure prevailing in the tank, the flow rate of an effluent gas from the tank, and the concentration of carbon dioxide in the effluent gas, where the pressure prevailing in the tank can be measured, for example, by an electric resistance-type pressure gage, an electric element-type pressure gage, or a hot-filament ionization-type gage; the flow rate of an effluent gas can be measured, for example, by a thermal mass flow meter; the concentration of carbon dioxide gas in an effluent gas can be measured, for example, by an infrared gas analyzer, or a process gas chromatography. The results of measurement can be obtained as electric signals, and thus the partial pressure of carbon dioxide gas in a cultivation tank and the amount of carbon dioxide gas can be rapidly calculated in a continuous on-line manner, and consequently the amount of microorganism cells in culture liquor can be calculated rapidly.

Figure 4:
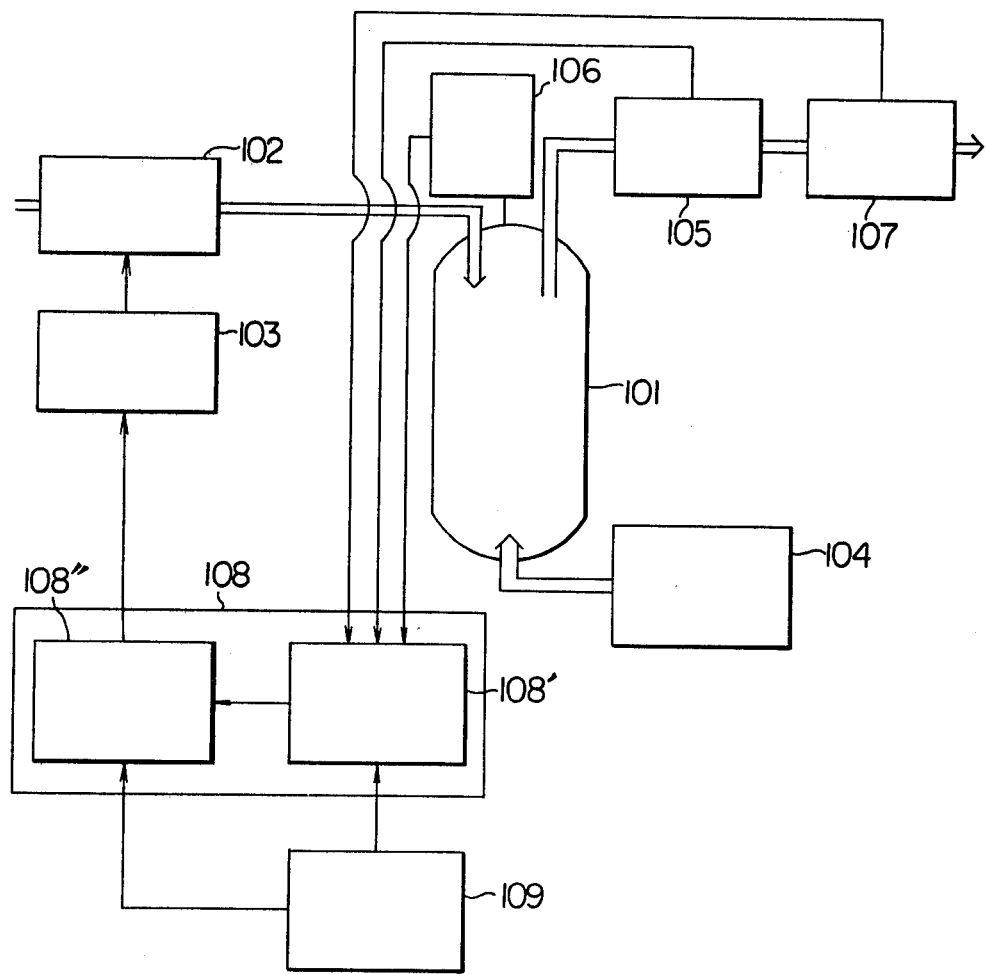
FIG. 4 is a schematic flow diagram showing one embodiment of the present apparatus.

One embodiment of the present invention will be described in detail below, referring to FIG. 4. A substrate is supplied into cultivation tank 101 by substrate supply means 102 capable of changing a supply rate of substrate and of being controlled by means 103 of adjusting the supply rate of substrate. Substrate supply means 102 can be, for example, a metering pump capable of changing a discharge rate, and means 103 for adjusting the supply rate of substrate can be, for example, a device of electrically adjusting a stroke span, which is interlocked by substrate supply means 102. Numeral 104 is a means for generating aeration gas such as a compressor, and numeral 105 is a means for measuring a flow rate of effluent gas such as a thermal mass flow meter capable of emitting the results of measurement as electrical signals.

Numeral 106 is a means for measuring a pressure prevailing in the cultivation tank, for example, an electrical resistance-type pressure gage. Numeral 107 is a means for measuring a concentration of carbon dioxide in the effluent gas from the cultivation tank, such as an infra-red gas analyzer. Numeral 108 is a calculating means, such as a microcomputer. Numeral 108' is a means for calculating an amount of microorganism cells, and numeral 108" is a means for determining an amount of the substrate to be supplied, which is determined on the basis of the results of calculation from means 108'. Numeral 109 is a means for setting numerical values, such as a key board. Flow from 109 to 108' gives the value k of the afore-mentioned equation, and flow from 109 to 108" gives a reference value for judging the appropriateness of an amount of the substrate to be supplied for the determined amount of microorganism cells.

The present process for controlling cultivation of microorganisms in the apparatus for cultivation comprising the above-mentioned means will be described below.

Seed microorganisms are placed in cultivation tank 101 before cultivation is started. Relations between the partial pressure of carbon dioxide gas in the cultivation tank and the ratio of the amount of propagated microorganism cells to the amount of produced carbon dioxide gas as obtained beforehand and the initial amount of microorganism cells are put into calculating means 108 from means 109 for setting numerical values.

Cultivation is carried out by supplying a gas from means 104 for generating aeration gas and a substrate from substrate supply means 102. The flow rate of an effluent gas from the cultivation tank, the concentration of carbon dioxide gas in the effluent gas, and the pressure prevailing in the cultivation tank are measured and the results of each measurement are put into calculating means 108 as electrical signals.

Means 108' for calculating the amount of microorganism cells calculates the partial pressure of carbon dioxide gas in the cultivation tank and the amount of carbon dioxide gas produced by microorganisms on the basis of the electrical signals from means 106 for measuring the pressure in the cultivation tank, means 105 for measuring the flow rate of the effluent gas from the cultivation tank, and means 107 for measuring the concentration of carbon dioxide gas in the effluent gas, and then calculates the amount of microorganism cells in culture liquor according to the afore-mentioned equation on the basis of the signals from means 109 for setting numerical values.

On the basis of the calculated amount of microorganism, means 108" for determining the amount of the substrate to be supplied emits a signal to means 103 for adjusting the amount of the substrate to be supplied to cells to increase the amount of the substrate to be supplied, if it is smaller for the amount of microorganism cells, or a signal to means 103 to decrease the amount of the substrate to be supplied, if it is larger for the amount of microorganism cells.

Means 103 for adjusting the amount of the substrate to be supplied controls substrate supply means 102 on the basis of the signal from means 108" for determining the amount of the substrate to be supplied.

The appropriateness of the amount of a substrate to be supplied for the amount of microorganism cells to be judged by means 108″ for determining the amount of a substrate to be supplied depends upon species of microorganisms to be cultivated, and cultivation tests should be made for the individual species of microorganisms in advance to define the standard for judgement.

When microorganisms are cultivated with an oxygen-enriched gas, it is preferable to carry out the cultivation in combination with controlling the concentration of dissolved oxygen. The control of the concentration of dissolved oxygen can be carried out by changing the flow rate of aeration gas, the concentration of oxygen in the aeration gas, and the number of revolution per minute of stirrer.

Examples of the present invention and Comparative Examples will be given below, but the present invention is never limited by these Examples.

EXAMPLE 1

Microorganism cells: bread yeast (*Saccharomyces cerevisiae*)

Culture medium: Aqueous solution of 30% molasses as sugar containing 11.1 g/l of urea and 4.1 g/l of phosphoric acid.

Cultivation conditions: The amount of microorganism cells was calculated by making the partial pressure of carbon dioxide gas in a mini-jar fermentor having a net capacity of 1 l as a cultivation tank 0.1 atm and the ratio of the amount of propagated microorganism cells to the amount of produced carbon dioxide gas 1.0 at a temperature of 30° C. and pH5 (see FIG. 3) to obtain the optimum conditions for cultivation beforehand. The above-mentioned culture medium was added to the mini-jar fermenter so that the amount of the sugar to be supplied for the amount of microorganism cells could be 0.3±0.1 g glucose/g dry cell·hr. The flow rate of aeration gas, the concentration of oxygen in the aeration gas and the number of revolution per minute of stirrer were changed, so that the concentration of dissolved oxygen could be kept at 2–5 mg/l. The initial amount of culture liquor was 350 ml, and the initial concentration of microorganism cells was 30 g dry cell/l.

Results: The amount of culture liquor reached 700 ml 12 hours after the start of cultivation, and the concentration of microorganism cells reached 83 g dry cell/l. The concentration of ethanol in the culture liquor could be kept at such low value as less than 150 mg/l throughout the cultivation and the yield based on the sugar was 45%.

EXAMPLE 2

Microorganism cells: bread yeast (*Saccharomyces cerevisiae*)

Culture medium: An aqueous solution of 30% glucose in potable water, containing 64.5 g/l of urea, 30 g/l of monosodium phosphate, 11.4 g/l of magnesium sulfate, 75 g/l of sodium citrate, 15 g/l of yeast extract and a vitamin solution.

Cultivation conditions: The amount of microorganism cells was calculated by making the partial pressure of carbon dioxide gas in a jar fermentor having a net capacity of 15 l as a cultivation tank 0.1 atm and the ratio of the amount of propagated microorganism cells to the amount of produced carbon dioxide gas 1.0 at a temperature of 30° C. and pH5. The above-mentioned culture medium was added to the jar fermenter so that the amount of the sugar to be supplied for the amount of microorganism cells could be 0.3±0.1 g glucose/g dry cell·hr. The flow rate of aeration gas, the concentration of oxygen in the aeration gas and the number of revolution per minute of stirrer were changed, so that the concentration of dissolved oxygen could be kept at 2–5 mg/l. The initial amount of culture liquor was 5 l, and the initial concentration of microorganism cells was 50 g dry cell/l.

Results: The amount of culture liquor reached 10 l, 12 hours after the start of cultivation, and the concentration of microorganism cells reached 95 g dry cell/l. The concentration of ethanol in the culture liquor could be kept at such low value as less than 150 mg/l throughout the cultivation, and the yield based on the sugar was 44%.

EXAMPLE 3

Microorganism cells: bread yeast (*Saccharomyces cerevisiae*)

Culture medium: Aqueous solution of 45% molasses as sugar containing 16.6 g/l of urea and 6.2 g/l of phosphoric acid.

Cultivation conditions: The amount of microorganism cells was calculated by making the partial pressure of carbon dioxide gas in a jar fermentor having a net capacity of 15 l as a cultivation tank 0.1 atm and the ratio of the amount of propagated microorganism cells to the amount of produced carbon dioxide gas 1.0 at a temperature of 30° C. and pH5. The above-mentioned culture medium was added to the jar fermenter so that the amount of the sugar to be supplied for the amount of microorganism cells could be 0.3±0.1 g glucose/g dry cell·hr. The flow rate of aeration gas, the concentration of oxygen in the aeration gas and the number of revolution per minute of stirrer were changed, so that the concentration of dissolved oxygen could be kept at 2–5 mg/l. The initial amount of culture liquor was 5 l, and the initial concentration of microorganism cells was 50 g dry cell/l.

Results: The amount of culture liquor reached 9.0 l, 12 hours after the start of cultivation, and the concentration of microorganism cells reached 120 g dry cell/l. The concentration of ethanol in the culture liquor could be kept at such low value as less than 150 mg/l throughout the cultivation, and the yield based on the sugar was 46%.

COMPARATIVE EXAMPLE (CONTROL BY ETHANOL CONCENTRATION)

Microorganism cells: bread yeast (*Saccharomyces cerevisiae*)

Culture medium: An aqueous solution of 32% molasses as sugar containing 11.8 g/l of urea and 4.4 g/l of phosphoric acid.

Cultivation conditions: The above-mentioned culture medium was added to a mini-jar fermentor having a net capacity of 1 l at a temperature of 30° C. and pH5, while observing an ethanol concentration as an index. That is, when the ethanol concentration was low, the amount of the culture medium was increased, whereas when it was high, the amount of the culture medium was decreased. The flow rate of aeration gas, the concentration of oxygen in the aeration gas and the number of revolution per minute of stirrer were changed, so that the concentration of dissolved oxygen could be kept at 2–5 mg/l. The initial amount of culture liquor was 0.35 l, and the initial concentration of microorganism cells was 57 g dry cell/l.

Results: The amount of culture liquor reached 700 ml, 15 hours after the start of cultivation, and the concentration of microorganism cells reached 94 g dry cell/l. The ethanol concentration in the culture liquor was changed to 200–4,700 mg/l throughout the cultivation, and the yield based on the sugar was as slow as 38%, because ethanol formation could not be prevented.

Furthermore, the present inventors conducted cultivation of, for example, bread yeast with an oxygen-enriched gas to determine what degree the partial pressure of carbon dioxide gas should be controlled to in aerobic cultivation of microorganisms, that is, the critical value of the partial pressure of carbon dioxide gas. The results are shown in FIG. 5, where relations between the partial pressure of carbon dioxide in an effluent gas from a cultivation tank and the yield of microorganism cells are shown. As is seen from FIG. 5, the yield of microorganism cells can be prevented from decrease by controlling the partial pressure of carbon dioxide gas in the effluent gas to 0.2 atm or less.

In the present invention, the aeration rate of oxygen-enriched gas, the concentration of oxygen and the number of revolutions per minute of stirrer are adjusted to control the partial pressure of carbon dioxide gas, but what is important in the aerobic cultivation of microorganisms is to maintain an appropriate amount of dissolved oxygen in culture liquor in addition to the control of the partial pressure of carbon dioxide in the effluent gas. For example, in the case of cultivation of bread yeast, the bread yeast undergoes aerobic metabolism when the amount of dissolved oxygen exceeds 0.2 ppm, and the microorganism cells are smoothly increased thereby. On the other hand, when the amount of dissolved oxygen is less than 0.2 ppm, the bread yeast undergoes anaerobic metabolism to produce ethanol, and the yield of microorganism cells is lowered thereby. When the amount of dissolved oxygen is too large, for example, more than 5 ppm, the excessively dissolved oxygen undesirably exerts an inhibiting effect upon the propagation. Thus, it is particularly important in aerobic cultivation to maintain the dissolved oxygen in an appropriate amount, that is, 0.2–5 ppm.

In the present invention, a correlation between the critical value of the partial pressure of carbon dioxide gas, for example, 0.2 atm in the case of bread yeast, in the relation between the yield of microorganism cells and the partial pressure of carbon dioxide gas, and the amount of dissolved oxygen is controlled by a combination of the aeration rate of oxygen-enriched gas, the concentration of the oxygen in the oxygen-enriched gas, and the number of revolutions per minute of stirrer. That is, when the partial pressure of carbon dioxide in an effluent gas is increased, the aeration rate of oxygen-enriched gas is increased to lower the partial pressure of carbon dioxide gas, but the amount of dissolved oxygen is increased. Thus, it is necessary to decrease the number of revolutions per minute of stirrer, or lower the concentration of oxygen in the aeration gas, or simultaneously change both number of revolutions per minute of stirrer and concentration of oxygen in the aeration gas. It is also possible to lower the pressure in the cultivation tank to lower the partial pressure of carbon dioxide gas in place of increasing the aeration rate to lower the partial pressure of carbon dioxide gas, but in that case, the amount of dissolved oxygen is lowered to the contrary, and thus it is necessary to increase the number of revolutions per minute of stirrer or increase the concentration of oxygen in the aeration gas.

Some microorganisms require a higher partial pressure of carbon dioxide in an effluent gas. In that case, operation should be carried out quite contrary to the operation for lowering the partial pressure of carbon dioxide gas. That is, since the amount of dissolved oxygen is decreased with decreasing rate of aeration, the number of revolutions per minute of stirrer or the concentration of oxygen in the aeration gas, or both should be increased. When the partial pressure of carbon dioxide gas is increased with increasing pressure in the cultivation tank, the amount of dissolved oxygen is increased, and thus it is necessary to decrease the number of revolutions per minute of stirrer or the concentration of oxygen in the aeration gas. It is possible to control the partial pressure of carbon dioxide in an effluent gas and the amount of dissolved oxygen at the same time by the afore-mentioned operations.

When the cultivation tank is not provided with a stirrer, that is, in the case of a bubbling tower, the effective control of cultivation can be carried out by conducting other controlling operations than that of changing the number of revolutions per minute of stirrer at the same time.

In the present invention, an oxygen cylinder and an air compressor can be used for changing the concentration of oxygen in an aeration gas, or an absorption-type oxygen separator or a cryogenic oxygen separator can be used.

Figure 6:
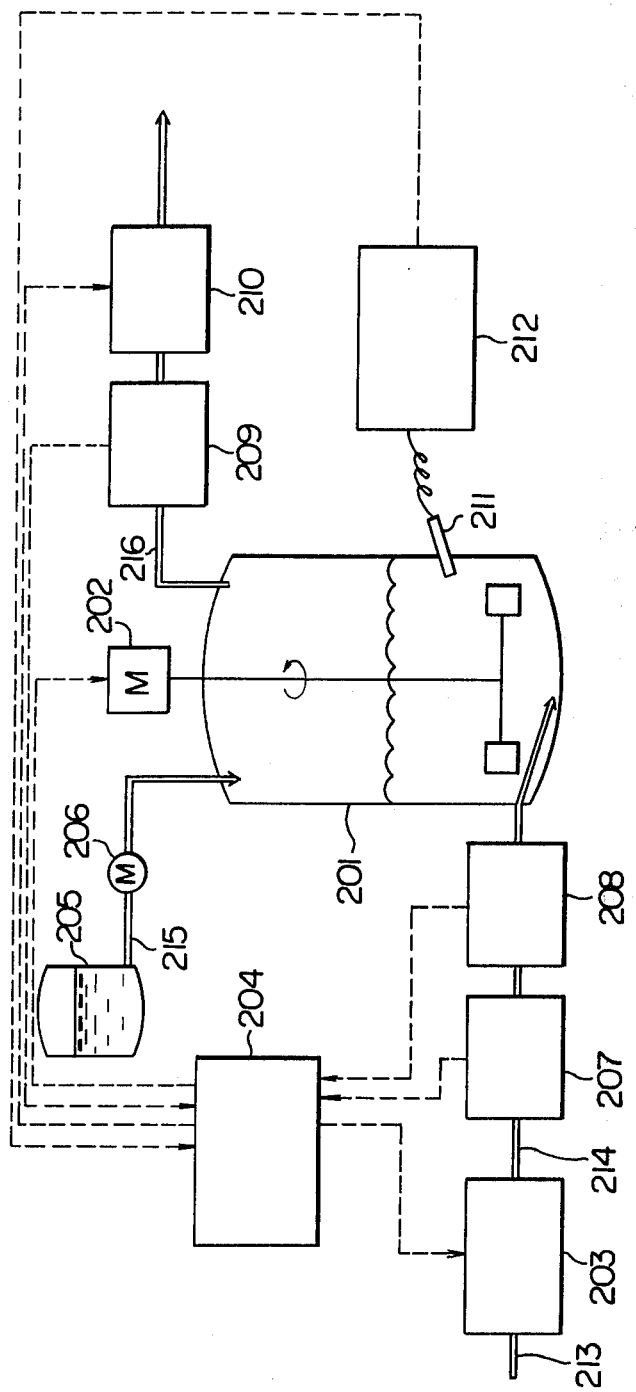
FIG. 6 is a schematic flow diagram showing one embodiment of an apparatus for controlling cultivation according to the present invention.

Another embodiment of the present invention will be described below, referring to FIG. 6, where a schematic flow diagram of an apparatus for controlling cultivation according to the present invention is shown. Numeral 201 is a cultivation tank, numeral 202 a stirrer, numeral 203 an oxygen separator, numeral 204 an electronic computer, numeral 205 a substrate tank, numeral 206 a substrate feed pump, numeral 207 an oxygen gas meter, numeral 208 an aeration rate meter, numeral 209 a $CO_2$ partial pressure meter, numeral 210 a pressure controller, numeral 211 a dissolved oxygen sensor, numerals 213–216 pipings.

Seed microorganisms are placed in cultivation tank 201, and a substrate is supplied thereto by substrate feed pump 206. Signals from dissolved oxygen sensor 211, $CO_2$ partial pressure meter 209 and aeration rate meter 208 are processed in electronic computer 204, which emits signals to oxygen separator 203, stirrer 202 and pressure controller 210 according to the predetermined control program to control the aeration rate, the pressure in the cultivation tank, and the number of revolutions per minute of stirrer or the concentration of oxygen in an aeration gas.

The present invention will be further described in detail below, referring to Examples, but the present invention is not limited by these Examples.

EXAMPLE 4

Microorganism cells: Bread yeast (Saccharomyces cerevisiae)

| Culture medium: | |
|---|---|
| glucose | 300 g |
| urea | 32.25 g |
| $NaHPO_4.2H_2O$ | 15 g |
| $MgSO_4.7H_2O$ | 5.7 g |

-continued

| Culture medium: | |
|---|---|
| KCl | 3.3 g |
| sodium citrate | 37.5 g |
| yeast extract | 7.5 g |
| vitamin solution* | 15 ml |
| mineral solution** | 15 ml |
| potable water to make the entire volume | 1 l |
| pH | 5.0 |

*The vitamin solution was prepared by adding 10.04 g of biotin, 0.08 g of vitamin $B_1$, 20 g of vitamin $B_6$, 1.0 g of calcium panthotate, and 20 g of inositol to distilled water to make the entire volume 1 l.
**The mineral solution was prepared by adding 0.05 g of $CaSO_4.5H_2O$, 0.8 g of $ZnSO_4.7H_2O$ and 0.3 g of $FeSO_4(NH_4)_2.6H_2O$ to distilled water to make the entire volume 1 l.

Figure 7:
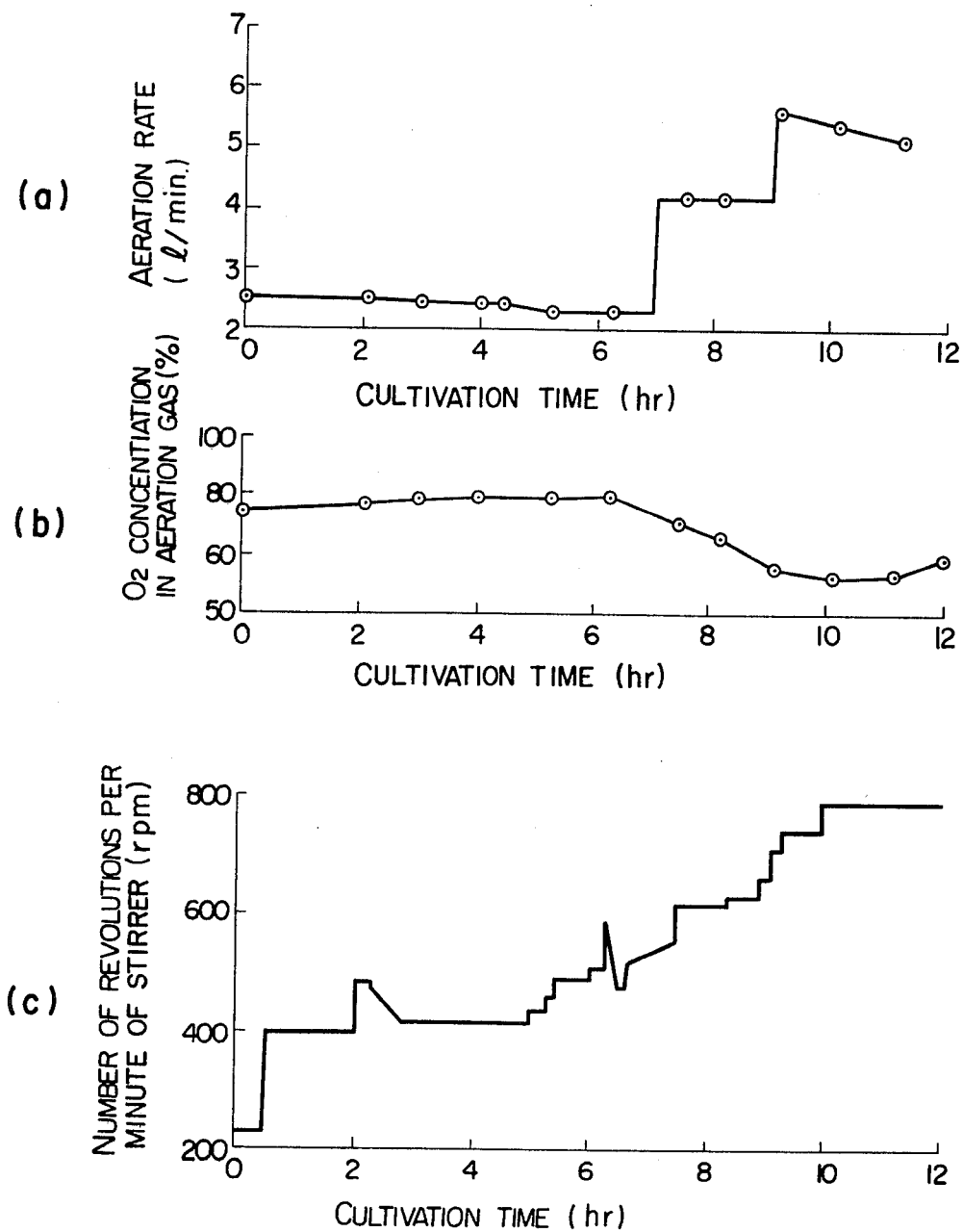
FIG. 7($a$) is a diagram showing relations between the cultivation time and the aeration rate of aeration gas according to Example 4.

Cultivation conditions: The microorganisms were cultivated in a jar fermentor having a net capacity of 15 l as a fermentation tank by adding thereto the aforementioned culture medium at a temperature of 30° C. and pH 5.0, while changing the aeration rate of aeration gas, the concentration of oxygen in the aeration gas, and the number of revolutions per minute of stirrer, as shown in FIG. 7, by means of an absorption-type oxygen separator so as to maintain the partial pressure of carbon dioxide in the effluent gas at 0.2 atm, and the amount of dissolved oxygen at 5 ppm. In FIG. 7(a), relations between the cultivation time and the aeration rate of aeration gas are shown. In FIG. 7(b), relations between the cultivation time and the concentration of oxygen in the aeration gas are shown. In FIG. 7(c), relations between the cultivation time and the number of revolutions per minute of stirrer are shown. The initial amount of culture liquor was 5.0 l, and the initial concentration of microorganism cells was 50 g/l.

Results: The partial pressure of carbon dioxide in the effluent gas could be maintained at 0.2±0.02 atm and the amount of dissolved oxygen at 5±1 ppm throughout the cultivation for 12 hours. The concentration of microorganism cells reached as high as 94 g/l, and the yield of microorganism cells was 0.44 g/g.

EXAMPLE 5

Cultivation was carried out with the same microorganism cells in the same culture medium as used in Example 4, while changing the aeration rate in a range of 10-15 l/min., the concentration of oxygen in the aeration gas in a range of 50-80%, and the number of revolutions per minute of stirrer in a range of 150-800 rpm by means of an absorption-type oxygen separator so as to maintain the partial pressure of carbon dioxide in the effluent gas at 0.03 atm and the amount of dissolved oxygen at 5 ppm. The initial amount of culture liquor was 5.0 l, and the initial concentration of microorganism cells was 50 g/l.

Results: The partial pressure of carbon dioxide in the effluent gas could be maintained at 0.03±0.002 atm and the amount of dissolved oxygen at 5±1 ppm throughout the cultivation for 12 hours. The concentration of microorganism cells reached as high as 95 g/l, and the yield of microorganism cells was 0.46 g/g. Comparative Example 2

Cultivation was carried out with the same microorganism cells in the same culture medium as used in Example 4, while changing the aeration rate in a range of 1-2 l/min., the concentration of oxygen in the aeration gas in a range of 50-80%, and the number of revolutions per minute of stirrer in a range of 400-800 rpm by means of an absorption-type oxygen separator so as to maintain the partial pressure of carbon dioxide in the effluent gas at 0.35 atm and the amount of dissolved oxygen at 5 ppm. The initial amount of culture liquor was 5.0 l, and the initial concentration of microorganism cells was 50 g/l.

Results: The partial pressure of carbon dioxide in the effluent gas could be maintained at 0.35±0.03 atm and the amount of dissolved oxygen at 5±1 ppm throughout the cultivation for 12 hours. The concentration of microorganism cells reached 82 g/l, and the yield of microorganism cells was 0.33 g/g. Under the higher partial pressure of carbon dioxide in the effluent gas, the yield of microorganism cells was lowered, and consequently the final concentration of microorganism cells was lowered.

Furthermore, the present inventors studied a process for controlling the concentration of dissolved oxygen easily and exactly, and found that it is preferable to control the number of revolutions per minute of stirrer as a first step, the partial pressure of oxygen in the aeration gas as a second step, and the aeration rate as a third step.

Figure 8:
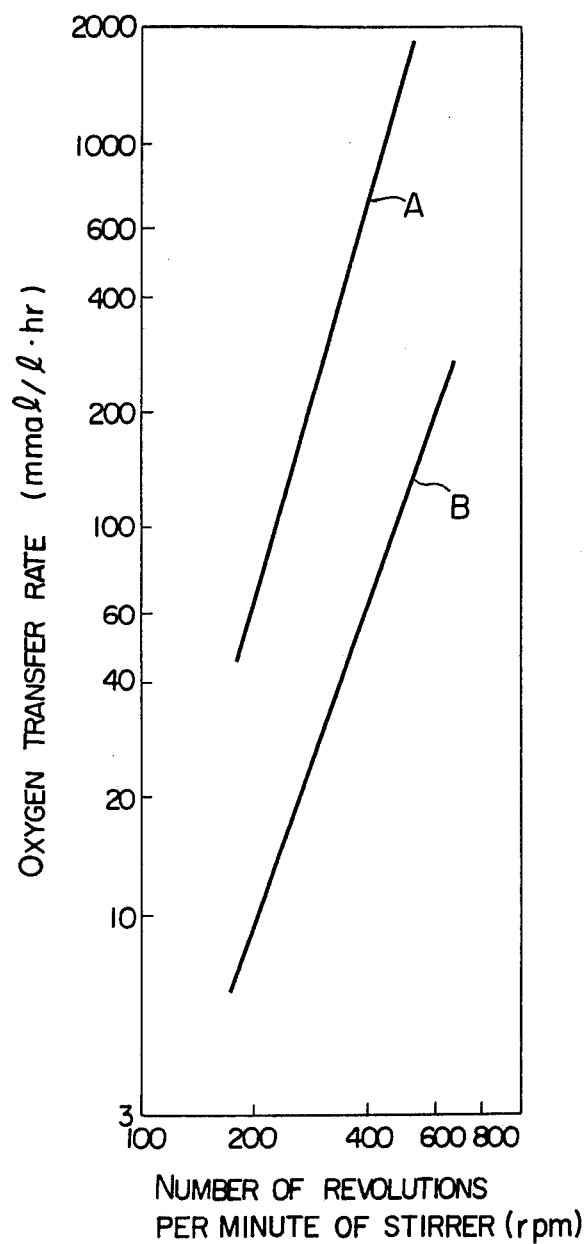
FIG. 8 is a diagram showing relations between the number of revolutions per minute of stirrer and the oxygen transfer rate.
Figure 9:
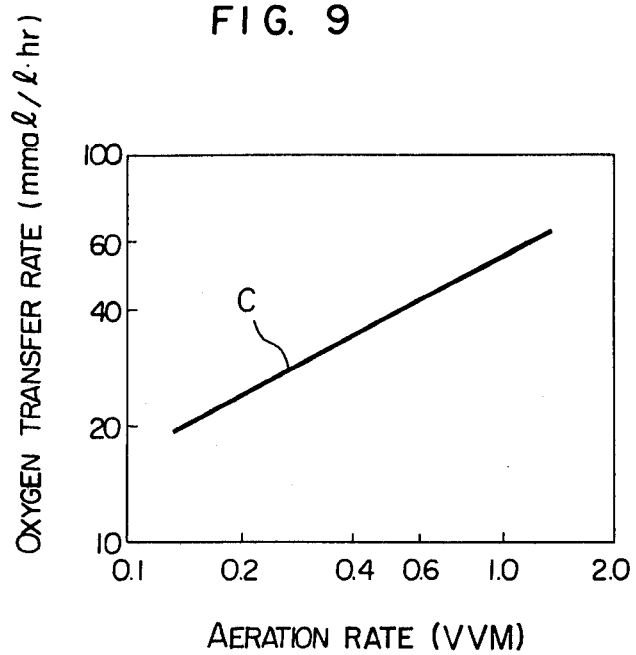
FIG. 9 is a diagram showing relations between the aeration rate and the oxygen transfer rate.

In FIGS. 8 and 9, results of measuring an oxygen transfer rate in a cultivation tank by sulfurous acid oxidation while changing the number of revolutions per minute of stirrer, the partial pressure of oxygen in an aeration gas and the aeration rate. In FIG. 8, symbol "A" stands for pure oxygen, and "B" air. In FIG. 9, symbol "C" stands for the number of revolutions per minute of stirrer being 350 rpm.

It can be seen from FIGS. 8 and 9 that, when the number of revolutions per minute of stirrer is doubled, the oxygen transfer rate is increased by more than 5-fold, and when the partial pressure of oxygen in the aeration gas is increased from 0.21 atm of air to 1 atm of pure oxygen, the oxygen transfer rate is increased by approximately 5-fold. On the other hand, even if the aeration rate is doubled, the oxygen transfer rate is not substantially increased. Thus, it can be seen that, in order to change the oxygen transfer rate in the culture liquor, it is most effective to change the number of revolutions per minute of stirrer, and to change the partial pressure of oxygen in the aeration gas and the aeration rate is less effective in this order.

In order to efficiently control the concentration of dissolved oxygen in culture liquor, it is preferable to effectively change the oxygen transfer rate, and thus when the concentration of dissolved oxygen in culture liquor is lowered, the number of revolutions per minute of stirrer should be increased as a first step. When the number of revolutions per minute of stirrer reaches the upper limit value as set, the partial pressure of oxygen in the aeration gas should be increased as a second step. When the partial pressure of oxygen in the aeration gas reaches the upper limit value as set, the aeration rate should be increased as a third step. On the other hand, when the concentration of dissolved oxygen in the culture liquor is higher than the value as set, the number of revolutions per minute of stirrer should be decreased as a first step. When the number of revolutions per minute of stirrer reaches the lower limit value as set, the partial pressure of oxygen in the aeration gas should be decreased as a second step. When the partial pressure of oxygen in the aeration gas reaches the lower limit value as set, the aeration rate should be decreased as a third step.

As compared with the conventional aeration only with air, an oxygen transfer rate as high as 2,000 m- mol/l·hr can be obtained with an oxygen-enriched gas, whereby cultivation at a high concentration of microorganism cells such as 20–50 g/l or higher, which has been so far impossible to conduct, can be carried out. Thus, the productivity of cultivation can be improved, and the amount of effluent culture liquor can be reduced thereby. Furthermore, it is possible to conduct cultivation requiring a high level of dissolved oxygen and cultivation in a highly viscous state having a possibility of decreasing the oxygen transfer rate due to a high viscosity.

The partial pressure of oxygen can be controlled according to either a procedure of changing the pressure in a cultivation tank, or a procedure of changing the concentration of oxygen in an aeration gas, or both. A higher partial pressure of oxygen can be obtained when both procedures are used.

The concentration of oxygen in an aeration gas can be changed by means of an oxygen gas cylinder, or an absorption-type oxygen separator, or a cryogenic oxygen separator.

The microorganisms applicable to the present invention include yeasts belonging to the genera Saccharomyces, Hansenula, Torulopsis, Pichia, Candida, Mycotorula, etc., bacteria belonging to genera Methylomonas, Pseudomonas, Alcaligenes, Bacillus, Corynabacterium, etc., actinomyces belonging to genera Nocardia, Streptomyces, etc., and molds belonging to genera Penicillium, Aspergillus, Trichoderma, etc.

Substrate for cultivation includes carbohydrates such as molasses, n-parafins, methanol, ethanol, acetic acid and fatty acids. Secondary raw materials other than the substrate include ammonium sulfate, urea, aqua ammonia, monopotassium phosphate, yeast extract, magnesium sulfate, ferrous sulfate, various vitamins, and minerals.

EXAMPLE 6

Microorganism cells: a strain belonging to the genus Hansenula
Culture medium:

| Substrate | |
|---|---|
| ethanol | 400 g |
| Secondary Raw Materials | |
| ammonium sulfate | 60 g |
| $KH_2PO_4$ | 30 g |
| $Na_2HPO_4$ | 30 g |
| $MgSO_4.7H_2O$ | 5 g |
| $FeSO_4.7H_2O$ | 0.2 g |
| $MnSO_4.4-6H_2O$ | 0.02 g |
| $CaCl_2.2H_2O$ | 0.02 g |
| thiamine | 4 mg |

Cultivation conditions:

The afore-mentioned culture medium was added to a jar fermenter having a net capacity of 50 l at a temperature of 35° C. and pH 3.5, and the concentration of dissolved oxygen was controlled by the number of revolutions per minute of stirrer, the partial pressure of oxygen in the aeration gas, and the aeration rate. The partial pressure of the aeration gas was changed by means of an air compressor and an oxygen gas cylinder. The initial amount of culture liquor was 15 l, and the initial concentration of microorganism cells 50 g/l.

Results: The concentration of dissolved oxygen could be maintained in a range of 2–4 ppm throughout the cultivation for 15 hours, whereby the concentration of microorganism cells reached as high as 110 g/l with the yield of microorganism cells being 0.70 g/g.

According to the present invention, the concentration of dissolved oxygen can be readily carried out, and thus cultivation at a high concentration of microorganism cell can be carried out with an effect of improving the productivity of a cultivation tank.

What is claimed is:

1. A process for controlling cultivation of microorganisms in culture medium in a cultivation tank comprising:
   (a) measuring pressure within the tank during cultivation;
   (b) measuring flow rate of effluent gas from the tank during cultivation;
   (c) measuring concentration of carbon dioxide in the effluent during cultivation;
   (d) calculating the partial pressure of carbon dioxide within the tank and the amount of carbon dioxide produced by microorganism growth based on measurements of (a), (b), and (c);
   (e) calculating the amount of propagated microorganisms according to the following equation:

$$X_2 = X_1 + K \Delta CO_2$$

wherein
   $X_2$ = amount of microorganisms in the cultivation tank at time $t_2$,
   $X_1$ = amount of microorganisms in the cultivation tank at time $t_1$,
   $\Delta CO_2$ = amount of carbon dioxide gas produced during the period between $t_1$ and $t_2$, and
   k = ratio of the amount of propagated microorganism cells to the amount of carbon dioxide gas produced, k being determined prior to the process by batch and continuous cultivation tests for each particular microorganism cultivated; and
   (f) supplying additional medium in accordance with the amount calculated at (e).

2. A process according to claim 1 wherein, when the microorganisms are cultivated with air or an oxygen-enriched gas, concentration of dissolved oxygen is also controlled.

3. A process according to claim 2, wherein the concentration of dissolved oxygen is controlled by at least one of:
   (a) aeration rate of oxygen-enriched gas aerating the cultivation tank;
   (b) concentration of oxygen in the oxygen enriched gas; and
   (c) number of revolutions per minute of a stirrer in the cultivation tank.

4. A process according to claim 2, wherein in an optimum relation between microbial yield, the partial pressure of carbon dioxide and the amount of dissolved oxygen, the partial pressure of carbon dioxide is controlled by the amount of dissolved oxygen, which is, in turn, controlled by at least one of:
   (a) aeration rate of oxygen enriched gas aerating the cultivation tank;
   (b) concentration of oxygen in the gas; and
   (c) number of revolutions per minute of a stirrer in the cultivation tank.

5. A process according to claim 4, wherein the partial pressure of carbon dioxide gas is kept at 0.2 atm or lower, and the amount of dissolved oxygen is kept at 0.2–5 ppm in the cultivation of bread yeast.

6. The process according to claim 1, wherein the results of measurements (a), (b), and (c) are continuously obtained as electrical signals which are detected by computer means to continuously calculate the number of microorganisms and to continuously provide the additional culture medium in accordance with the number of microorganisms.

7. A process for aerobically controlling cultivation of microorganisms in culture medium in a cultivation tank wherein in an optimum relation between microbial yield, partial pressure of carbon dioxide within the tank and amount of dissolved oxygen in the culture medium, the partial pressure of carbon dioxide is controlled by the amount of dissolved oxygen which is in turn controlled by at least one of:

(a) aeration rate of oxygen-enriched gas aerating the cultivation tank, (b) concentration of oxygen in the oxygen enriched gas, and (c) number of revolutions per minute of a stirrer in the cultivation tank, so that when the concentration of dissolved oxygen becomes lower than a set value, the concentration is increased by at least one of:

first increasing the number of revolutions per minute of the stirrer, secondly, increasing the partial pressure of the oxygen in the aeration gas, and thirdly, increasing the aeration rate;

and when the concentration of dissolved oxygen becomes higher than the set value, the concentration is decreased by at least one of:

first decreasing the number of revolutions per minute of the stirrer, secondly decreasing the partial pressure of oxygen in the aeration gas, and thirdly decreasing the aeration rate; and further wherein the partial pressure of carbon dioxide is maintained at no greater than 0.2 atm and the amount of dissolved oxygen is maintained at 0.2–5 p.p.m.

8. A process according to any one of claims 1 or 7 wherein the microorganisms are bread yeast.

* * * * *